(12) United States Patent
Fujimoto (10) Patent No.: US 10,374,116 B2
(45) Date of Patent: Aug. 6, 2019

(54) LIGHT RECEIVING AND EMITTING ELEMENT MODULE AND SENSOR DEVICE

(71) Applicant: KYOCERA Corporation, Kyoto-shi, Kyoto (JP)

(72) Inventor: Naoki Fujimoto, Higashiomi (JP)

(73) Assignee: KYOCERA Corporation, Kyoto (JP)

( * ) Notice: Subject to any disclaimer, the term of this patent is extended or adjusted under 35 U.S.C. 154(b) by 0 days.

(21) Appl. No.: 15/569,595

(22) PCT Filed: Apr. 27, 2016

(86) PCT No.: PCT/JP2016/063219
§ 371 (c)(1),
(2) Date: Oct. 26, 2017

(87) PCT Pub. No.: WO2016/175246
PCT Pub. Date: Nov. 3, 2016

(65) Prior Publication Data
US 2018/0301585 A1    Oct. 18, 2018

(30) Foreign Application Priority Data

Apr. 27, 2015  (JP) .................................. 2015-090056

(51) Int. Cl.
*H01L 31/12* (2006.01)
*G01N 21/17* (2006.01)
(Continued)

(52) U.S. Cl.
CPC ............. *H01L 31/12* (2013.01); *G01N 21/17* (2013.01); *G01S 7/4813* (2013.01);
(Continued)

(58) Field of Classification Search
CPC ....................................................... H01L 31/12
(Continued)

(56) References Cited

U.S. PATENT DOCUMENTS

| 2006/0086911 | A1 | 4/2006 | Charrier et al. |
| 2013/0313415 | A1* | 11/2013 | Tseng .................. H01L 31/0203 250/216 |
| 2017/0294426 | A1* | 10/2017 | Uchida .................. H01L 25/167 |

FOREIGN PATENT DOCUMENTS

| EP | 0585186 A2 | 3/1994 |
| JP | S56-34354 U | 4/1981 |

(Continued)

OTHER PUBLICATIONS

Machine translation of Taniguchi et al., JP H7-273365, Oct. 20, 1995.*

(Continued)

*Primary Examiner* — Hsin Yi Hsieh
(74) *Attorney, Agent, or Firm* — Procopio Cory Hargreaves and Savitch LLP (57) ABSTRACT

A light receiving and emitting element module includes a wiring substrate; a light emitting element and a light receiving element which are disposed on the wiring substrate; and a lens member having a lens portion, a support portion configured to support the lens portion disposed above the light emitting element and the light receiving element and a column disposed on a lower surface of the support portion, wherein a tip end of the column is in contact with an upper surface of the wiring substrate.

10 Claims, 4 Drawing Sheets

(51) Int. Cl.
  *H01L 31/0216* (2014.01)
  *H01L 31/0232* (2014.01)
  *H01L 33/58* (2010.01)
  *G01S 17/02* (2006.01)
  *H01L 25/16* (2006.01)
  *H01L 31/0203* (2014.01)
  *H01L 31/173* (2006.01)
  *G01S 7/481* (2006.01)

(52) U.S. Cl.
  CPC .......... *G01S 17/026* (2013.01); *H01L 25/167* (2013.01); *H01L 31/0203* (2013.01); *H01L 31/02164* (2013.01); *H01L 31/02325* (2013.01); *H01L 31/173* (2013.01); *H01L 33/58* (2013.01); *G01N 2201/061* (2013.01); *H01L 2224/48091* (2013.01); *H03K 2217/94108* (2013.01)

(58) Field of Classification Search
  USPC .......................................................... 257/82
  See application file for complete search history.

(56) References Cited

FOREIGN PATENT DOCUMENTS

| | | |
|---|---|---|
| JP | H7-273365 A | 10/1995 |
| JP | H8-88399 A | 4/1996 |
| JP | 2006-135314 A | 5/2006 |
| JP | 2006-203111 A | 8/2006 |
| JP | 2014-127684 A | 7/2014 |
| JP | WO 2016047545 A1 * | 3/2016 ........... H01L 25/167 |

OTHER PUBLICATIONS

International Search Report dated Jul. 12, 2016, issued by Japan Patent Office for International Application No. PCT/JP2016/063219.

* cited by examiner

LIGHT RECEIVING AND EMITTING ELEMENT MODULE AND SENSOR DEVICE

TECHNICAL FIELD

The present invention relates to a light receiving and emitting element module and a sensor device.

BACKGROUND ART

A sensor device has conventionally been proposed that detects a property of an object by irradiating light from a light emitting element to the object and receiving reflected light from the object by a light receiving element.

For example, Japanese Unexamined Patent Publication JP-A 2006-203111 proposes a sensor device in which a light receiving element and a light emitting element are disposed on a substrate and a lens is disposed above the light receiving element and the light emitting element.

SUMMARY OF THE INVENTION

A light receiving and emitting element module according to an embodiment of the invention includes a wiring substrate; a light emitting element and a light receiving element which are disposed on the wiring substrate; and a lens member having a lens portion, a support portion configured to support the lens portion disposed above the light emitting element and the light receiving element and a column disposed on a lower surface of the support portion, wherein a tip end of the column is in contact with an upper surface of the wiring substrate.

A sensor device according to an embodiment of the invention includes the above-described light receiving and emitting element module; and a control circuit electrically connected to the light receiving and emitting element module and configured to control the light receiving and emitting element module, the sensor device irradiating light from the light emitting element to an object and detecting a property of the object according to an output value from the light receiving element which is outputted according to reflected light from the object.

DESCRIPTION OF EMBODIMENTS (Light Receiving and Emitting Element Module)

Hereinafter, an example of an embodiment of the light receiving and emitting element module of the invention will be described with reference to the drawings. The present embodiment is not limited to the following embodiment.

While the light receiving and emitting element module of the invention may be used with any direction as the upper side or the lower side, in the description, for the sake of convenience, an orthogonal coordinate system (X, Y, Z) is defined, and a term such as an upper surface or a lower surface is used with the positive side in the Z axis direction as the upper side.

Figure 1A:
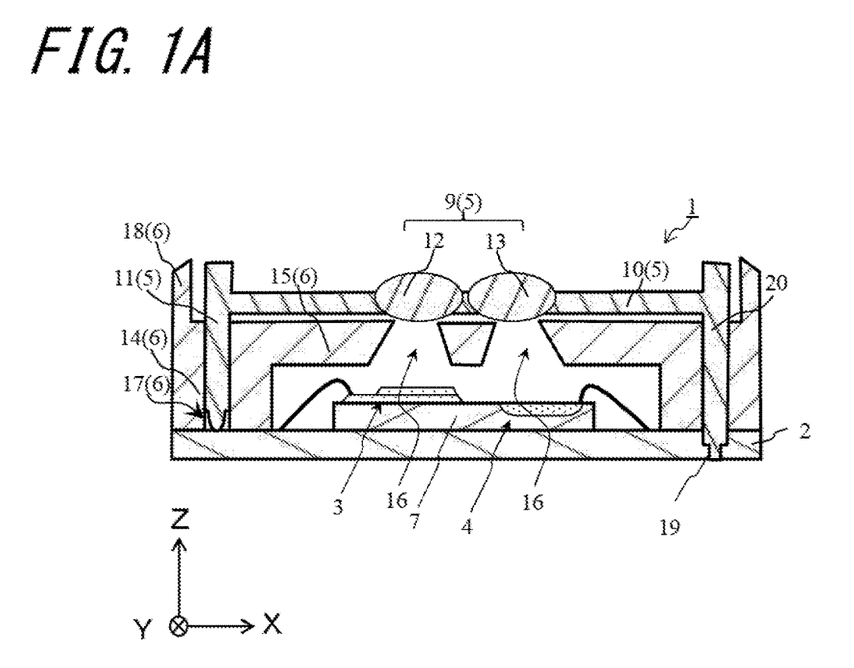
FIG. 1A is a schematic cross-sectional view showing a light receiving and emitting element module according to an embodiment of the invention.
Figure 1B:
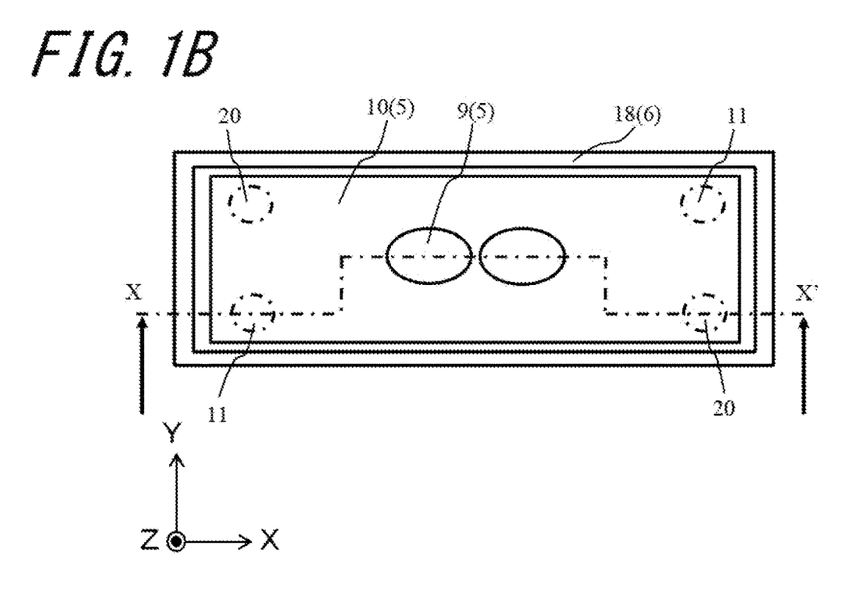
FIG. 1B is a schematic top view showing the light receiving and emitting element module according to the embodiment of the invention. The cross-sectional view of FIG. 1A is a cross-sectional view when the light receiving and emitting element module is taken along the alternate long and short dash line shown in FIG. 1B.

Regarding a light receiving and emitting element module 1, as shown in FIGS. 1A and 1B, the light receiving and emitting element module 1 having a wiring substrate 2, and a light emitting element 3 and a light receiving element 4 which are disposed on the wiring substrate 2 can irradiate light from the light emitting element 3 to an object and receive light reflected at the object by the light receiving element 4. As a consequence, the light receiving and emitting element module 1 can sense the surface condition and the like of the object.

The light receiving and emitting element module 1 is disposed, for example, on an image forming apparatus such as a copier or a printer to enable the detection of position information, distance information, density information and the like of the object such as toner or a medium. The light receiving and emitting element module 1 may also be disposed, for example, on a machine tool or the like to sense the surface condition of a workpiece. The light receiving and emitting element module 1 is considered to be disposed not only on the above-mentioned examples but also on various apparatuses.

The light receiving and emitting element module 1 further has a lens member 5. The lens member 5 can condense the light from the light emitting element 3 and guide it to the object. The lens member 5 can also condense the light reflected at the object and guide it to the light receiving element 4. The light receiving and emitting element module 1 further has a light shield 6. The light shield 6 can reduce unintended light (stray light) received by the light receiving element 4.

The wiring substrate 2 has the light emitting element 3 and the light receiving element 4 disposed thereon, and can support the light emitting element 3 and the light receiving element 4. The wiring substrate 2 is electrically connected to an external apparatus and, for example, applies a bias voltage to the light emitting element 3 and the light receiving element 4.

The wiring substrate 2 is in the shape of, for example, a rectangle. As the wiring substrate 2, for example, a resin substrate or a ceramic substrate may be used. The wiring substrate 2 of the present disclosure is a resin substrate. In the description, the resin substrate refers to a substrate in which an insulating material in the wiring substrate 2 is made of a resin material. The ceramic substrate refers to a substrate in which the insulating material in the wiring substrate 2 is made of a ceramic material. The wiring substrate 2 may be formed by a conventionally known method.

The light emitting element 3 and the light receiving element 4 of the present disclosure have the same semiconductor substrate 7. In other words, the light emitting element 3 and the light receiving element 4 are formed using one semiconductor substrate 7 as a base. As a consequence, the light emitting element 3 and the light receiving element 4 can be disposed close to each other, so that the sensing performance of the light receiving and emitting element module 1 can be improved.

The light emitting element 3 and the light receiving element 4 of the present disclosure are integrally disposed on the wiring substrate 2 through one semiconductor substrate 7. While the light receiving and emitting element module 1 of the present disclosure is provided with one light emitting element 3 and one light receiving element 4, the light receiving and emitting element module 1 may be provided with more than one light emitting element 3 and more than one light receiving element 4.

The semiconductor substrate 7 has a semiconductor material of one conductivity type. The semiconductor substrate 7 of the present disclosure is formed of the semiconductor material of one conductivity type. For the semiconductor substrate 7 of the present disclosure, for example, an n-type Si (silicon) substrate is used. That is, the semiconductor substrate 7 is formed by doping an n-type impurity into the Si substrate. As the n-type impurity for the Si substrate, for example, P (phosphorus), N (nitrogen), As (arsenic), Sb (antimony) or Bi (bismuth) is used. In the description, the one conductivity type is the n type, whereas the reverse conductivity type is the p-type.

Figure 2A:
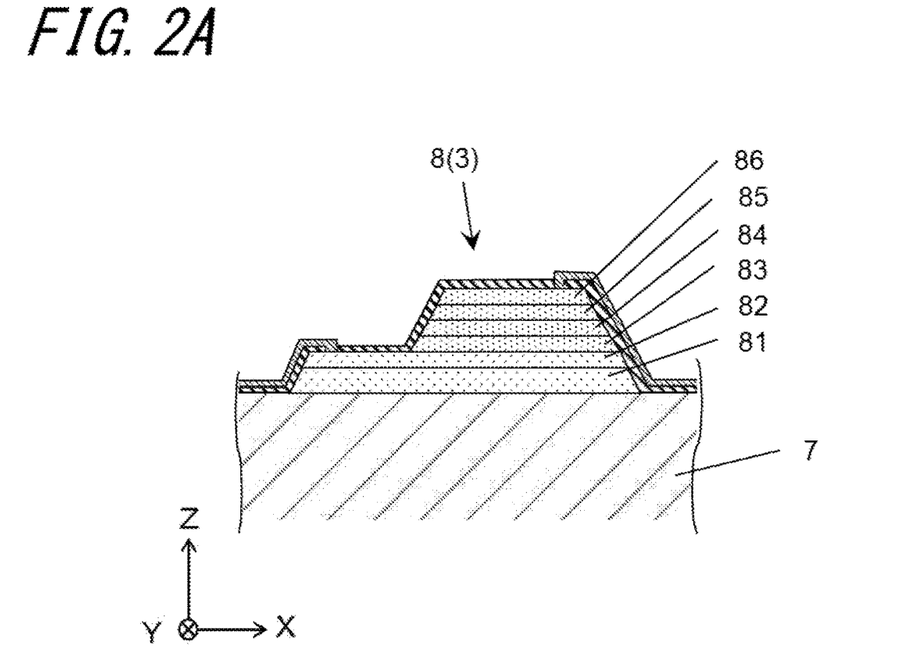
FIG. 2A is a cross-sectional view of a light emitting element constituting the light receiving and emitting element module shown in FIG. 1.

The light emitting element 3 is formed, as shown in FIG. 2A, by laminating a plurality of semiconductor layers 8 on an upper surface of the semiconductor substrate 7. The plurality of semiconductor layers 8 may be formed, for example, by epitaxial growth on the semiconductor substrate 7 using an MOCVD (metal-organic chemical vapor deposition) apparatus.

The plurality of semiconductor layers 8 have a buffer layer 81 laminated on the upper surface of the semiconductor substrate 7. The buffer layer 81 can buffer the difference in lattice constant at the interface between the semiconductor substrate 7 and the plurality of semiconductor layers 8. The buffer layer 81 is formed of, for example, GaAs (gallium arsenide).

The plurality of semiconductor layers 8 have an n-type contact layer 82 laminated on an upper surface of the buffer layer 81. The n-type contact layer 82 has a cathode electrode of the light emitting element 3 formed on an upper surface thereof. The n-type contact layer 82 can reduce the contact resistance with the electrode. The n-type contact layer 82 may be formed, for example, by doping an n-type impurity into GaAs. As the n-type impurity for the GaAs, for example, Si or Se (selenium) is used.

The plurality of semiconductor layers 8 have an n-type clad layer 83 laminated on the upper surface of the n-type contact layer 82. The n-type clad layer 83 can confine positive holes in an active layer 84 described later. The n-type clad layer 83 may be formed, for example, by doping an n-type impurity into AlGaAs (aluminum gallium arsenide). As the n-type impurity for the AlGaAs, for example, Si or Se is used.

The plurality of semiconductor layers 8 have the active layer 84 laminated on an upper surface of the n-type clad layer 83. The active layer 84 can emit light by concentration and recombination of carriers such as positive holes and electrons. That is, the active layer 84 can function as a light emitting layer. The active layer 84 is formed of, for example, AlGaAs.

The plurality of semiconductor layers 8 have a p-type clad layer 85 laminated on an upper surface of the active layer 84. The p-type clad layer 85 can confine electrons in the active layer 84. The p-type clad layer 85 may be formed, for example, by doping a p-type impurity into AlGaAs. As the p-type impurity for the AlGaAs, for example, Zn (zinc), Mg (magnesium) or C (carbon) is used.

The plurality of semiconductor layers 8 have a p-type contact layer 86 laminated on an upper surface of the p-type clad layer 85. The p-type contact layer 86 has an anode electrode of the light emitting element 3 formed on an upper surface thereof. The p-type contact layer 86 can reduce the contact resistance with the electrode. The p-type contact layer 86 may be formed, for example, by doping a p-type impurity into AlGaAs. In order to reduce the contact resistance with the electrode, the p-type contact layer 86 is formed so that the carrier density thereof is higher than that of the p-type clad layer 85.

Figure 2B:
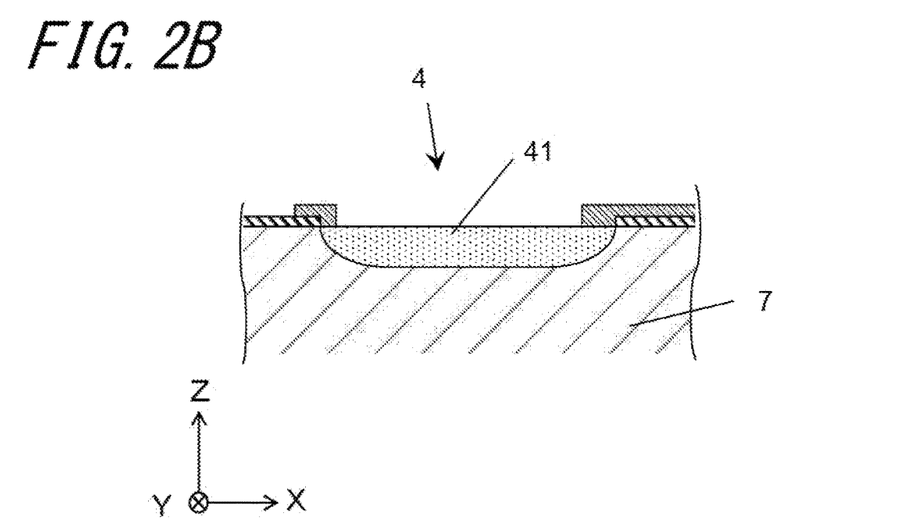
FIG. 2B is a cross-sectional view of a light receiving element constituting the light receiving and emitting element module shown in FIG. 1A.

As shown in FIG. 2B, a p-type semiconductor region 41 is provided in the upper surface of the semiconductor substrate 7. As a consequence, a p-n junction is formed at the interface between the n-type semiconductor substrate 7 and the p-type semiconductor region 41 to enable the formation of the light receiving element 4. The p-type semiconductor region 41 is formed by doping a p-type impurity into the semiconductor substrate 7. Since the semiconductor substrate 7 of the present disclosure is an Si substrate, examples of the p-type impurity include Zn, Mg, C, B (boron), In (indium) and Se.

The lens member 5 has a lens portion 9, a support portion 10 and a column 11. The lens portion 9 is a portion through which light passes, and can function as a lens. The support portion 10 can support the lens portion 9. The column 11 is provided on a lower surface of the support portion 10, and can support the support portion 10.

The lens member 5 is formed of, for example, a light-transmittable material. The lens member 5 is formed of, for example, a thermosetting resin such as silicone resin, urethane resin and epoxy resin, plastics such as thermoplastic resin such as polycarbonate resin and acrylic resin, or sapphire and inorganic glass. The lens member 5 is formed, for example, by injection molding or otherwise. In the lens member 5, only the lens portion 9 have a light-transmitting property, and the support portion 10 and the column 11 do not necessarily have to have a light-transmitting property.

The lens portion 9 can condense the light emitted from the light emitting element 3 and the light reflected at the object and guide them. The lens portion 9 has a first lens 12 which condenses the emitted light of the light emitting element 3 and a second lens 13 which condenses the reflected light from the object. The first lens 12 and the second lens 13 of the present disclosure are each, for example, a convex lens, a spherical lens or an aspherical lens.

The support portion 10 has a function of holding the lens portion 9. The support portion 10 is, for example, of a plate-like shape. The support portion 10 may support the lens portion 9 by being integrated with the lens portion 9 or may support the lens portion 9 by the first lens 12 and the second lens 13 of the lens portion 9 being fit in the support portion 10. Here, "integrated" indicates that the lens portion 9 and the support portion 10 are continuous without any joint. That is, at this time, the lens portion 9 and the support portion 10 are simultaneously formed of the same material by one process.

The column 11 supports the lens portion 9 and the support portion 10, and consequently can support the lens member 5. The lens portion 9 and the support portion 10 of the lens member 5 are disposed above the light emitting element 3 and the light receiving element 4. The column 11 is disposed on the lower surface of the support portion 10, and a tip end of the column 11 is in contact with an upper surface of the wiring substrate 2. That is, the lens member 5 is disposed by making the column 11 abut on the wiring substrate 2. As a consequence, the distance between the lens portion 9, and the light emitting element 3 and the light receiving element 4 can be made an appropriate distance by keeping the length of the column 11 constant. Consequently, the occurrence of positional displacement in the vertical direction (the Z axis direction) among the lens portion 9, and the light emitting element 3 and the light receiving element 4 can be reduced, so that the sensing performance of the light receiving and emitting element module 1 can be improved.

The positioning of the lens member 5 in the vertical direction is performed by the column 11 which is a columnar member. As a consequence, the influence of the form of the upper surface of the wiring substrate 2 can be reduced since the area of contact with the wiring substrate 2 is small compared with a case where the positioning in the vertical direction is performed, for example, by a frame-like member. Consequently, the occurrence of positional displacement in the vertical direction can be more effectively reduced. The column 11 of the present embodiment is, for example, cylindrical.

A tip end surface of the column 11 may be a convexly curved surface. As a consequence, the influence of the form of the upper surface of the wiring substrate 2 can be effectively reduced since the contact between the column 11 and the wiring substrate 2 can be made close to point contact. Consequently, the occurrence of positional displacement in the vertical direction can be more effectively reduced. Moreover, by forming the tip end surface as a curved surface, the occurrence of chipping of the tip end of the column 11 can be reduced compared with a case where the tip end thereof is pointed.

The first lens 12, the second lens 13, the support portion 10 and the column 11 may be integrated. That is, the members constituting the lens member 5 may be integrated. In other words, the first lens 12, the second lens 13, the support portion 10 and the column 11 may be such that the components are continuous without any boundaries at contact positions between the respective components. As a consequence, variation in the positional relationship among the components can be reduced compared with when the components of the lens member 5 are, for example, separately made and then, bonded together to form the lens member 5.

The lens member 5 may have a plurality of column 11 and may be disposed so as to sandwich the light emitting element 3 and the light receiving element 4. As a consequence, the height between the light emitting element 3 and the lens portion 9 and the height between the light receiving element 4 and the lens portion 9 can be controlled by the columns 11. In the present embodiment, the plurality of columns 11 may be disposed on a diagonal line of the rectangular wiring substrate 2.

Since the light emitting element 3 and the light receiving element 4 of the present disclosure are formed on one semiconductor substrate 7, variation in the positional relationship between the light emitting element 3 and the light receiving element 4 can be reduced compared with a case where the light emitting element 3 and the light receiving element 4 are separately disposed on the wiring substrate 2.

The light shield 6 is disposed between the lens member 5 and the wiring substrate 2 so as to surround the light emitting element 3 and the light receiving element 4. As a consequence, the light shield 6 can reduce receipt of the stray light by the light receiving element 4 as mentioned above.

The light shield 6 is formed of, for example, commodity plastics such as polypropylene resin (PP), polystyrene resin (PS), polyvinyl chloride resin (PVC), polyethylene terephthalate resin (PET) or acrylonitrile butadiene styrene resin (ABS), engineering plastics such as polyamide resin (PA) or polycarbonate resin (PC), super engineering plastics such as liquid crystal polymer, or a metal material such as aluminum (Al) or titanium (Ti). The light shield 6 may be formed, for example, by injection molding or otherwise.

Figure 3:
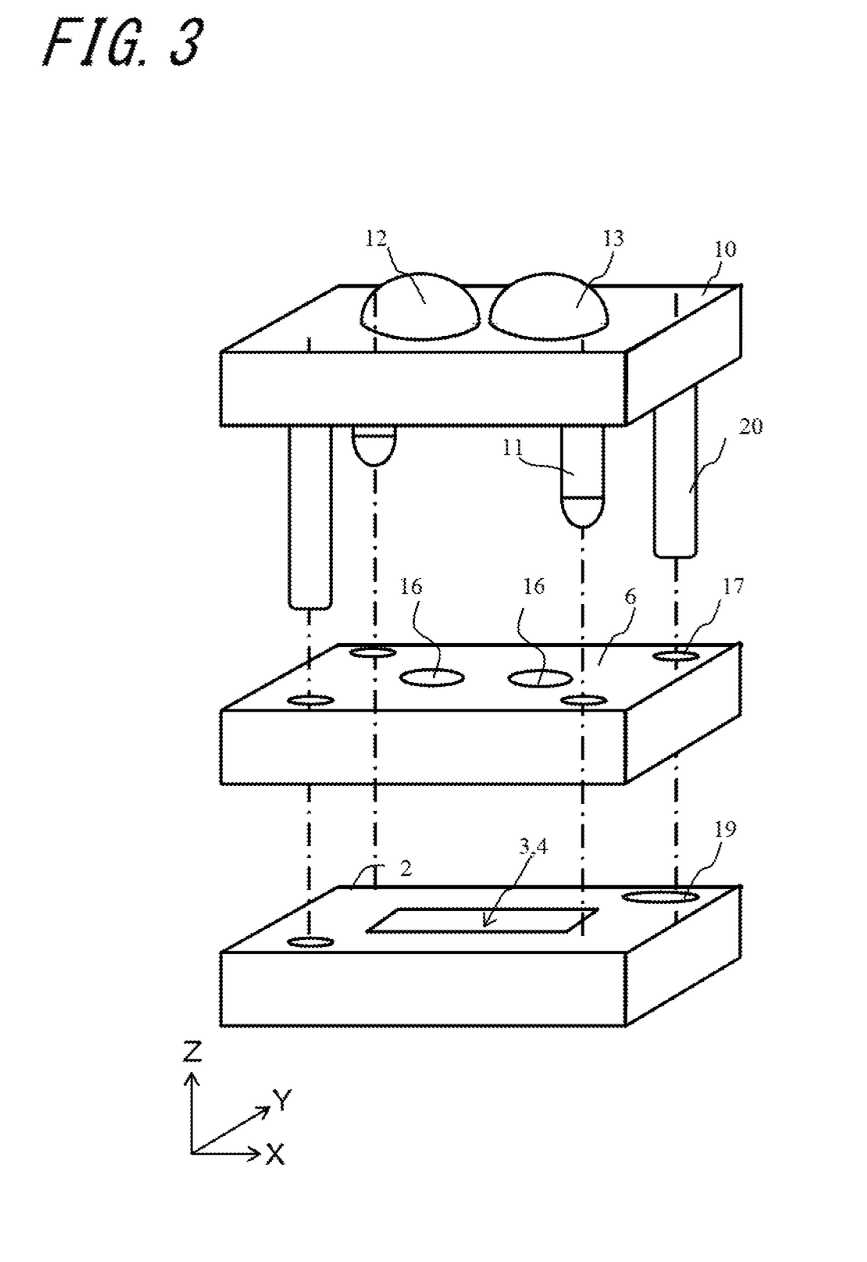
FIG. 3 is a perspective view where the light receiving and emitting element module according to the embodiment of the invention is disassembled for each component.

The light shield 6 has a wall portion 14 and a lid portion 15. The wall portion 14 is a frame-like member which surrounds the light emitting element 3 and the light receiving element 4. The lid portion 15 is provided on an inner surface of the wall portion 14 in the vicinity of an upper end portion so as to cover an area surrounded by the wall portion 14. That is, the wall portion 14 has an upper surface, and the lid portion 15 is provided so as to constitute an upper surface of the light shield 6 together with the wall portion 14. The lid portion 15 has a light passing portion 16 disposed on an optical path extending from the light emitting element 3 to the first lens 12 and on an optical path extending from the second lens 13 to the light receiving element 4. The light passing portion 16 of the present disclosure is a plurality of holes.

The wall portion 14 has the upper surface and a lower surface, and is provided with one through hole 17 having openings disposed in the upper surface and the lower surface. In the through hole 17, the column 11 of the lens member 5 is disposed. In other words, the column 11 is inserted in the through hole 17. As a consequence, the column 11 can be protected since the column 11 is covered with the light shield 6, and the occurrence of breakage of the column 11, for example, due to an external impact can be reduced.

Tip end portions of the plurality of columns 11 may be tapered toward the tip ends thereof. As a consequence, the insertion of the lens member 5 into the light shield 6 is facilitated at the time of manufacture of the light receiving and emitting element module 1, so that the production efficiency of the light receiving and emitting element module 1 can be improved.

The upper surface of the light shield 6 may be apart from the lower surface of the support portion 10 of the lens member 5. That is, a gap may be provided between the upper surface of the light shield 6 and the lower surface of the support portion 10. As a consequence, the occurrence of upthrust of the lens member 5, for example, due to thermal expansion of the light shield 6 or the like can be reduced. Consequently, the distance between the lens member 5, and the light emitting element 3 and the light receiving element 4 can be easily maintained, which facilitates the maintenance of the sensing performance of the light receiving and emitting element module 1.

When the light receiving and emitting element module 1 is viewed from above, an outer edge of the light shield 6 may be disposed outside an outer edge of the lens member 5. An upper surface of an outer edge portion of the light shield 6 may have a convex portion 18 protruding upward. As a consequence, the lens member 5 can be protected, for example, from external stress. The convex portion 18 of the present disclosure is continuous so as to surround the support portion 10.

The lens member 5 may be fixed via an adhesive on an inner surface of the convex portion 18 of the light shield 6 and a side surface of the support portion 10. As a consequence, an amount of adhesive entering between the lower surface of the support portion 10 and an upper surface of the lid portion 15 of the light shield 6 can be reduced, so that the occurrence of positional displacement in the vertical direction of the lens member 5 due to thermal expansion of the adhesive can be reduced.

The wiring substrate 2 may have a plurality of hole portions 19 having an opening disposed in the upper surface of the wiring substrate 2. The lens member 5 may further have a plurality of second columns 20 provided on the lower surface of the support portion 10, tip ends of the second columns 20 being inserted in the hole portions 19 of the wiring substrate 2, respectively, in addition to the columns 11 (hereinafter, referred to as first columns 11). As a consequence, not only the position alignment in the vertical direction can be performed by the first columns 11 but also the position alignment of the lens portion 9 with the light emitting element 3 and the light receiving element 4 in the planar direction (the direction of the XY plane) can be performed by the plurality of second columns 20. All of the members including the plurality of second columns 20 of the lens member 5 may be integrated.

The plurality of second columns 20 of the present disclosure are disposed on a diagonal line of the wiring substrate 2, and the light emitting element 3 and the light receiving element 4 are disposed in between the plurality of second columns 20. On one diagonal line of the wiring substrate 2 of the present disclosure, two first columns 11 are disposed, and on the other diagonal line, two second columns 20 are disposed. The first columns 11 of the present disclosure are disposed closer to the central portion of the wiring substrate 2 than the second columns 20.

Moreover, the plurality of second columns 20 may be inserted in the through hole 17 of the light shield 6. As a consequence, the position alignment of the light shield 6 in the planar direction can also be performed. As a consequence, by inserting the second columns 20 in the hole portions 19, the position alignment of the light emitting element 3, the light receiving element 4, the lens member 5 and the light shield 6 can be performed with the hole portions 19 of the wiring substrate 2 as one reference. Consequently, since a plurality of components can be collectively disposed in one structure based on an absolute reference, the sensing performance can be improved compared with a case where a plurality of members are separately disposed while the relative positions thereof are aligned, based on a multiplicity of references.

Tip end portions of the plurality of second columns 20 may be tapered toward the tip ends thereof. As a consequence, the insertion of the lens member 5 into the light shield 6 or the hole portions 19 is facilitated at the time of manufacture of the light receiving and emitting element module 1, so that the production efficiency of the light receiving and emitting element module 1 can be improved.

A diameter of the through hole 17 of the light shield 6 in which the first column 11 is inserted may be larger than a thickness of the first column 11. As a consequence, since the first columns 11 are not involved in the positioning of the light shield 6 in the planar direction, the positioning of the light shield 6 is performed only by the second columns 20. Consequently, since the first columns 11 are not restrained by the lens member 5, the occurrence of bending of the first columns 11 due to application of a force to the first columns 11 by the lens member 5 can be reduced.

The configurations of the hole portions 19 of the wiring substrate may be all the same or may be different. That is, the configuration of one of the plurality of hole portions 19 may be with a size having more play than the others. This facilitates assembly when the second columns 20 of the same configuration are inserted. Here, it is desirable that one of the plurality of hole portions 19 provided with a size having more play is not provided with play uniformly in the X and Y directions but is provided with more play only in one direction. For example, as shown in FIG. 3, one of the two hole portions 19 is provided with an oval shape having play only in a longitudinal direction of the wiring substrate 2 (the X axis direction in the figure). Thereby, the positional displacement can be reduced.

The plurality of hole portions 19 may be arranged asymmetrically with each other. As a consequence, the occurrence of insertion of the plurality of second columns 20 into wrong hole portions 19 can be reduced.

While the position alignment of the light shield 6 is performed by using the through hole 17 in the present embodiment, it may be performed by forming a protruding portion and a recessed portion on either the upper surface of the light shield 6 or on the lower surface of the support portion 10.

(Sensor Device)

Figure 4:
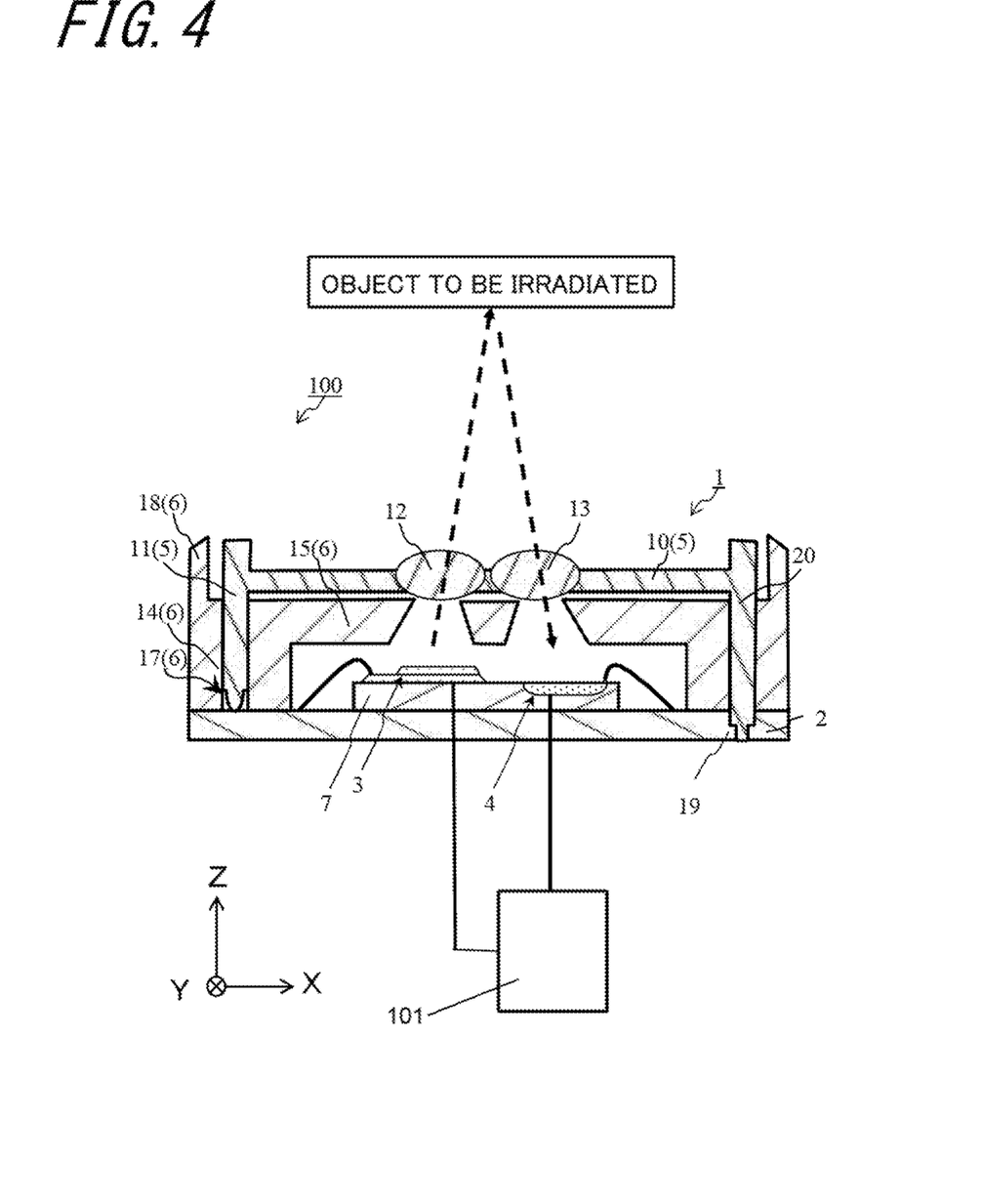
FIG. 4 is a cross-sectional view schematically showing a sensor device according to an embodiment of the invention.

Next, a sensor device 100 provided with the light receiving and emitting element module 1 will be described. As shown in FIG. 4, the sensor device 100 of the present embodiment has the light receiving and emitting element module 1 and a control circuit 101 electrically connected to the light receiving and emitting element module 1. The control circuit 101 controls the light receiving and emitting element module 1. The control circuit 101 includes, for example, a driving circuit for driving the light emitting element 3, an arithmetic circuit for processing the output (current, voltage or the like) from the light receiving element 4 or a communication circuit for communicating with an external apparatus. Dashed arrows shown in FIG. 4 illustrate paths of the light emanating from the light emitting element 3.

REFERENCE SIGNS LIST

1: Light receiving and emitting element module
2: Wiring substrate
3: Light emitting element
4: Light receiving element
5: Lens member
6: Light shield
7: Semiconductor substrate
8: Plurality of semiconductor layers
9: Lens portion
10: Support portion
11: Column
12: First lens
13: Second lens
14: Wall portion
15: Lid portion
16: Light passing portion
17: Through hole
18: Convex portion
19: Hole portion
20: Second column
100: Sensor device
101: Control circuit

The invention claimed is:
1. A light receiving and emitting element module, comprising:
   a wiring substrate;
   a light emitting element and a light receiving element which are disposed on the wiring substrate; and
   a lens member comprising a lens portion, a support portion configured to support the lens portion disposed above the light emitting element and the light receiving element and a plurality of columns disposed on a lower surface of the support portion,
the plurality of columns including a plurality of first columns and a plurality of second columns,
the plurality of first columns being positioned with the light emitting element and the light receiving element interposed therebetween, and tip ends of the first columns being in contact with and above a top flat surface of the wiring substrate,
the plurality of second columns being positioned with the light emitting element and the light receiving element interposed therebetween, and tip ends of the second columns being disposed in a plurality of hole portions whose openings are disposed in the top flat surface of the wiring substrate.

2. The light receiving and emitting element module according to claim 1, wherein the lens portion, the support portion, the plurality of first columns and the plurality of second columns are integrated in the lens member.

3. The light receiving and emitting element module according to claim 1, wherein a tip end surface of each of the plurality of first columns of the lens member is a convexly curved surface.

4. The light receiving and emitting element module according to claim 1, further comprising:
a light shield, which is disposed between the lens member and the wiring substrate, is surrounding the light emitting element and the light receiving element, and the light shield comprises a wall portion having frame-like and including an upper surface and a lower surface,
wherein the wall portion of the light shield comprises through holes including openings disposed in the upper surface and the lower surface of the wall portion, and
the plurality of first columns and the plurality of second columns are disposed in the through holes.

5. The light receiving and emitting element module according to claim 4,
wherein the upper surface of the light shield is apart from the lower surface of the support portion of the lens member.

6. The light receiving and emitting element module according to claim 4,
wherein when the light receiving and emitting element module is viewed from above, an outer edge of the light shield is disposed outside an outer edge of the lens member,
an upper surface of the outer edge of the light shield further comprises a convex portion protruding upward, and
the lens member is fixed to the light shield via an adhesive on a side surface of the support portion of the lens member and an inner surface of the convex portion.

7. The light receiving and emitting element module according to claim 6, wherein the convex portion is surrounding the support portion of the lens member.

8. The light receiving and emitting element module according to claim 1,
wherein the wiring substrate is rectangular in a plan view thereof, and
the plurality of hole portions are disposed on a diagonal line of the wiring substrate, and the light emitting element and the light receiving element are disposed in between the plurality of hole portions.

9. The light receiving and emitting element module according to claim 8,
wherein the second columns are fixed via an adhesive on inner surfaces of the hole portions.

10. A sensor device, comprising:
the light receiving and emitting element module according to claim 1; and
a control circuit electrically connected to the light receiving and emitting element module and configured to control the light receiving and emitting element module,
the sensor device irradiating light from the light emitting element to an object and detecting a property of the object according to an output value from the light receiving element which is outputted according to reflected light from the object.

* * * * *